United States Patent
Johnson et al.

(10) Patent No.: US 8,799,008 B2
(45) Date of Patent: Aug. 5, 2014

(54) SYSTEM AND METHOD TO MANAGE DELIVERY OF HEALTHCARE TO A PATIENT

(75) Inventors: Christopher Johnson, Clifton Park, NY (US); Kunter Akbay, Niskayuna, NY (US); Andrew Day, Pewaukee, WI (US); GianFranco Doretto, Albany, NY (US); Peter Tu, Niskayuna, NY (US); Onur Dulgeroglu, Niskayuna, NY (US); Marcia Peterson, Elgin, IL (US); David Toledano, Round Lake, NY (US)

(73) Assignee: General Electric Company, Schenectady, NY (US)

( * ) Notice: Subject to any disclaimer, the term of this patent is extended or adjusted under 35 U.S.C. 154(b) by 1266 days.

(21) Appl. No.: 12/239,270

(22) Filed: Sep. 26, 2008

(65) Prior Publication Data
US 2009/0089093 A1 Apr. 2, 2009

Related U.S. Application Data

(60) Provisional application No. 60/976,582, filed on Oct. 1, 2007.

(51) Int. Cl.
*G06Q 10/00* (2012.01)
*G06F 7/60* (2006.01)
*G06G 7/58* (2006.01)
*G06F 9/45* (2006.01)
*A61B 5/00* (2006.01)
*G06F 19/00* (2011.01)

(52) U.S. Cl.
USPC .................................. 705/2; 705/3

(58) Field of Classification Search
USPC ........................................... 705/2, 3
See application file for complete search history.

(56) References Cited

U.S. PATENT DOCUMENTS

2002/0165733 A1* 11/2002 Pulkkinen et al. ................ 705/2
2004/0100377 A1* 5/2004 Brackett et al. .......... 340/539.13
2005/0283382 A1* 12/2005 Donoghue et al. ................ 705/2

* cited by examiner

*Primary Examiner* — Sean K Hunter
(74) *Attorney, Agent, or Firm* — Hanley, Flight & Zimmerman, LLC

(57) ABSTRACT

A system and method to manage delivery of healthcare via a plurality of resources to a patient is provided. The system and method track and output a signal representative of a location of at least one of a series of resources relative to a control volume associated with the patient, acquire at least one signal representative of detecting ingress or egress of at least one of the plurality of resources relative to the control volume; and output a first signal representative of one of a series of milestones as defined in a predetermined protocol in response to detecting ingress or egress of at least one of the resources relative to the control volume.

18 Claims, 4 Drawing Sheets

US 8,799,008 B2

SYSTEM AND METHOD TO MANAGE DELIVERY OF HEALTHCARE TO A PATIENT

CROSS REFERENCE TO RELATED APPLICATIONS

This application claims priority to Provisional Application No. 60/976,582 entitled "Method To View Biometrical Information and Dynamically Adapt Schedule and Process Interdependencies with Clinical Process Decisioning" filed Oct. 1, 2007, and is hereby incorporated herein by reference in its entirety.

BACKGROUND OF THE INVENTION

This invention generally relates to a system for and method to manage delivery healthcare to a patient.

Infections can result in operation of hospitals or clinics or other healthcare environments in association with interaction of the healthcare provider with multiple patients, deliverables, or surfaces over a time interval or at the surgical point of care. Not only can infections be harmful to the health of the patient, but also increase costs to treat the patient and can harm a reputation of a healthcare institution.

BRIEF DESCRIPTION OF THE INVENTION

The subject matter described herein provides a system and method to reduce the probability of infection rates associated with delivery of healthcare in a healthcare environment. The subject matter of the system and method described herein also enhances visualization of the protocol in delivery of healthcare to the patient without unduly interrupting or interfering with the performance of the staff delivering the healthcare.

The above-mentioned shortcomings, disadvantages and problems are addressed by the embodiments described herein in the following description.

An embodiment of a method to manage delivery of healthcare via a series of resources to a patient is provided. The method comprises the steps of tracking and outputting a signal representative of a location of at least one of the plurality of resources relative to a control volume associated with the patient; acquiring at least one signal representative of detecting ingress or egress of at least one of the series of resources relative to the control volume; and outputting a first signal representative of one of a plurality of milestones as defined in a predetermined protocol in response to detecting ingress or egress of at least one of the series of resources relative to the control volume.

An embodiment of a system to manage delivery of healthcare via a series of resources to a patient is provided. The system comprises at least one tracking system operable to generate a signal representative of a location of at least one of the series of resources relative to a control volume associated with the patient, and a controller in communication with the tracking system. The controller includes a processor in communication with a memory, the processor operable to execute a plurality of program instructions stored in the memory. The plurality of program instructions are representative of the steps of acquiring at least one signal representative of detecting ingress or egress of at least one of the plurality of resources relative to the control volume; outputting a first signal representative of one of a plurality of milestones as defined in a predetermined protocol in response to detecting ingress or egress of at least one of the plurality of resources relative to the control volume.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The following is generally description subject matter is described a perioperative example is presented. It can be appreciated that monitored activity may occur in many venues for deliver of care (e.g., home, ambulatory or inpatient settings).

Figure 1:
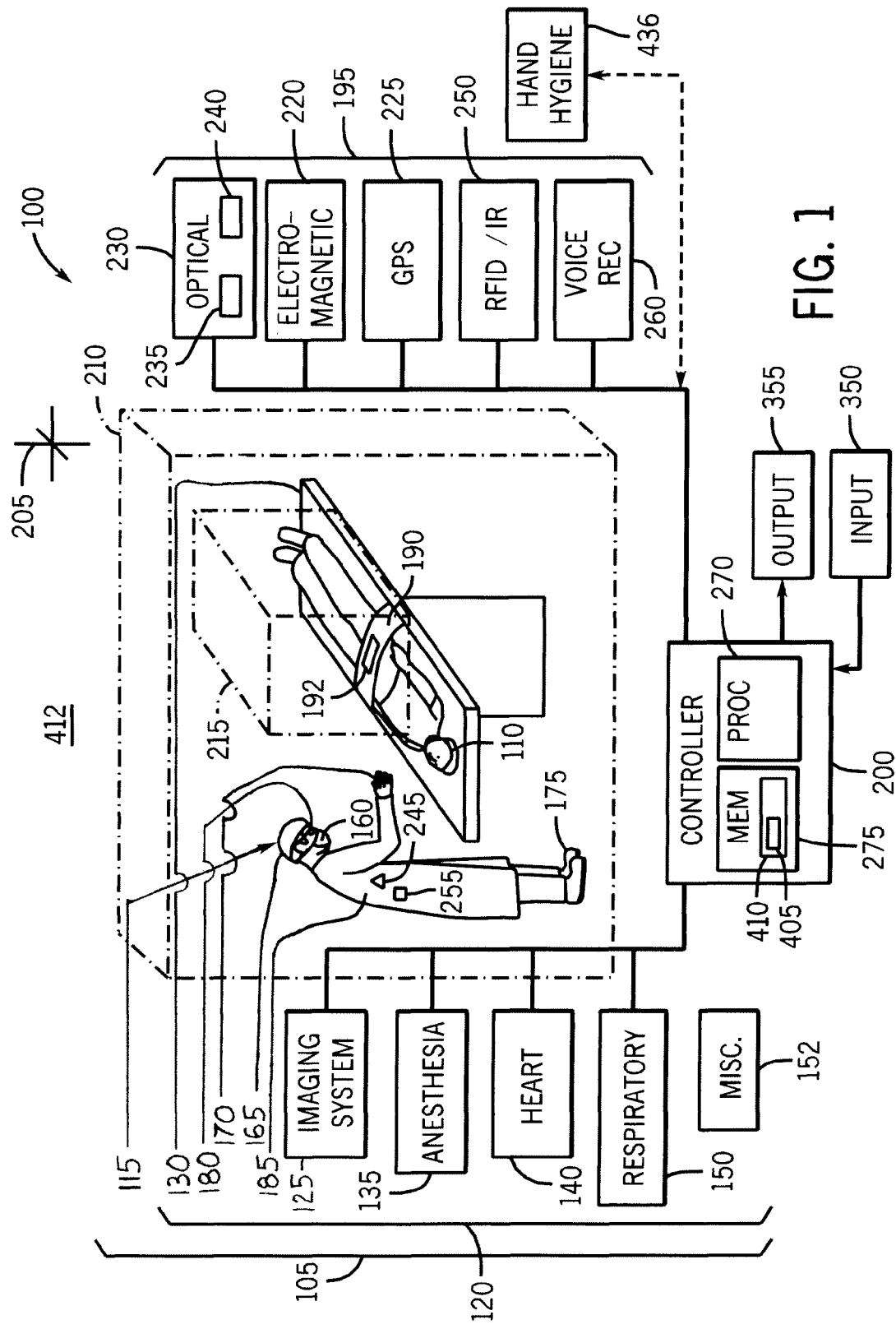
FIG. 1 shows a schematic block diagram of an embodiment of a system to manage delivery of healthcare to a patient.

FIG. 1 illustrates an embodiment of system 100 to manage resources 105 in the delivery of healthcare to a patient 110. The resources 105 can include personnel or staff 115 (e.g., surgeon, clinician, nurse, anesthetist, technician, etc.) and medical deliverables 120 (e.g., imaging system 125, table 130, anesthesiology system 135, heart monitor system 140, respiratory monitor system 150, miscellaneous items 152 such as medications/anesthesia or contrast agents or instruments or disposables or consumables, etc.) in the delivery of healthcare (e.g., medical procedure) to the patient 110.

An embodiment of the imaging system 125 can include a mobile radiological X-ray system having a gantry with a mobile C-arm in support of a radiation source and detector operable to generate a radiological image of a subject (not shown). Yet, the imaging system 125 can be also fixed to the ground with miscellaneous moving components. Although a mobile radiological imagine system is shown, it should be understood that the type (e.g., X-ray, magnetic resonant imaging (MRI), computed tomography (CT), ultrasound, fluoroscopic, endoscopic, laparoscopic, etc.) of imaging systems 100 can vary.

The table 130 can be located for the surgeon to perform the surgical procedure on the subject, as well as to position the subject be imaged by the imaging system 125. The table 130 can be configured to elevate, pan, tilt, or cradle so as to position the imaged subject in a desirable fashion for imaging by the imaging system 125.

Other medical deliverables 120 can include mechanical or electromechanical devices or clothing that may be employed in a conventional manner in performing a medical procedure.

For example, the surgeon attire can typically include a surgical mask 160, a cap 165, gloves 170, booties 175, protective eyewear 180, and a gown 185. The patient 110 can be covered with at least one drape 190 arranged with an opening for the surgical site 192 on the patient 110. The type and number of medical deliverables 120 can vary.

A tracking system 195 can be operable to periodically or continuously track or monitor a static or change in location or position or status of the miscellaneous resources 105, apparatus or personnel described above, including the location of the surgeon or other staff 115 and the patient 110. The embodiment of the tracking system 120 can be in communication (e.g., wireless, wired, etc.) with a controller 200. The controller 200 can also connected in communication (e.g., wireless, wired, etc.) with the imaging system 125 other medical apparatuses (e.g., anesthesia machine, heart rate monitor, blood pressure monitor, voice recognition, clinical systems and health information systems, etc.) located in or outside the surgical suite and employed in the deliver of healthcare to the patient.

An embodiment of the tracking system 195 can be operable to periodically or continuously measure a location or position or change thereof relative to a reference 205. An embodiment of the reference 205 can include a control volume 210 or a sterile zone 215 (e.g., two- or three-dimensional space encompassing or surrounding or located over the surgical site or other location of interest) defined for the surgical procedure on the patient 110. An embodiment of the tracking system 195 can be operable to define the control volume 210 or the sterile zone 215 located therein, and to track or detect the ingress or egress of resources 105 to or from such. For example, assume the control volume 210 or sterile zone 215 can be shaped as a rectangular box having corners defined by three-dimensional coordinates relative to the reference 205 (e.g., a fixed point on the table 130. Of course, the type (e.g., static or dynamic) and location of the reference 205 can vary. The control volume 210 or sterile zone 215 can be registered relative to the fixed reference 205 prior to the delivery of healthcare to the patient 110, and can be periodically updated during the delivery procedure. The number, shapes, and dimensions of the control volume 205 or sterile field 215 can vary.

As shown in FIG. 1, an embodiment of the tracking system 195 employs electromagnetic technology 220 to measure the location or movement of the resources 105. The tracking system 195 can include an arrangement of transmitters in electromagnetic communication with receivers to measure and output the signal representative of the identifier and the location of the resources 105 for communication to the controller 200. It should be understood that the number, type and location of the electromagnetic transmitters or receivers can vary.

The signal output from the electromagnetic technology 220 of the tracking system 195 can also include position data indicative of an orientation (e.g., an angle of rotation) or change thereof of the resources 105 relative to the reference 205 (e.g., vertical, horizontal, etc.). In an embodiment, the tracking system 195 can electromagnetically measure a location and orientation of the respective resources 105 capable of being tracked in such a manner. Also, the tracking system 195 can be configured to electromagnetically measure a position or change thereof of a movable component of the resources 105 and to output a signal representative thereof with an identifier for communication to the controller 200.

The illustrated embodiment of the tracking system 195 can further comprise transmitters and receivers configured to communicate with a satellite (e.g., global positioning technology 225) so as to measure a precise location or movement of the resources 105 or moveable components thereof for communication to the controller 200.

The illustrated embodiment of the tracking system 195 can further include optic technology 230 to measure the location or orientation or change thereof of the resources (or moveable components thereon) for communication to the controller 200. One embodiment of the optic technology 230 can include a pair of camera devices 235 and 240 operable to detect and generate a signal representative of an identifier and a measured location and orientation of optical markers 245 located on the resources 105. An example of the optical markers 245 can include graphic symbols or reflective material or patterns of unique identification or orientation (e.g., three spaced-apart graphic representations) that can be detected and tracked with the camera devices 235 and 240. Yet, the type of optical markers 245 can vary.

Another embodiment of the tracking system 195 can employ at least one camera 235, 240 operable to identify the resources 105 according to optical detecting and recognizing resources 105 according to association of predetermined shapes, patterns, color contrasts, reflections, etc. or combination thereof acquired and stored in the system 100, and thereby operable to track movement of the resources 105 accordingly. Embodiments of the orientation of multiple cameras 235, 240 can be orthogonal (one camera looking down from ceiling and one camera looking across horizon) or in parallel relation to one another, or a combination thereof, yet the orientation can vary. Further, although two cameras 235, 240 are shown, the number and type (e.g., video) of cameras and combination thereof can vary.

Another embodiment of the tracking system 195 can include a radio frequency (RF) or infrared (IR) identification system 250. The RF/IR identification system 250 can include RFID transmitters coupled in communication with RFID receivers to track location and movement of resources (e.g., staff, medical deliverables, etc.) that may enter to or from the surgical suite. In a like manner, the RF/IR identification system 250 can otherwise or also include IR technology that can be employed independently of or in combination with the RFID technology to track movement of tags 255 coupled to resources 105 of interest.

The tracking system 195 can further include a voice recognition system 260. An embodiment of the voice recognition system 260 can be operable to record speech of the surgeon or staff 115 and to perform voice recognition so as to translate speech to alphanumeric language in a digital or analog context for communication to the controller 200. The voice recognition system 260 can further be operable to parse the alphanumeric language for key words or phrases or fragments thereof for communication to the controller 200 for comparison to templates that include keywords, phrases, or fragments thereof representative of protocol or steps of the medical procedure being performed on the patient 110. The system may utilize optics, computer vision and can request confirmation feedback on the system's reasoning as to what process step is being observed by said system. An example confirmation may be a rule engine providing text to a speech generator asking the surgeon if s/he is in fact at a given stem in a protocol as the system has reasoned.

Although one embodiment of the tracking system 195 is described above, it should be understood that the number and types (e.g., electromagnetic, optical, rF/IR, accelerometers, voice recognition, etc. or combination thereof) of tracking technologies and combinations thereof to locate positions or movement of resources 105 or moveable components thereon can vary.

The controller 200 can be in wired or wireless communication with one or more of the medical deliverables 120 or the tracking system 195 so as to track movement or consumption or disposal of the resources 105 between various states or locations. The communication of the controller 200 with the tracking system 195 can be via a wireless connection (e.g., radio frequency, etc.) or wired connection (e.g., communication bus, etc.) or combination thereof. Communication can be direct, or over an Internet network or an Ethernet network or a local area network (LAN).

An embodiment of the controller 200 can include a computer in a desktop configuration or laptop configuration or central workstation or kiosk or server or remote workstation. Yet, the type of controller 200 can vary. The controller 200 generally includes one or more processors 270 in communication with a memory 275 having a computer-readable storage medium (e.g., compact disc (CD), DVD, memory stick, random access memory (RAM), random operating memory (ROM), etc.). The storage medium is generally operable to receive and record a plurality of programmable instructions for execution by the processor 155.

Figure 2:
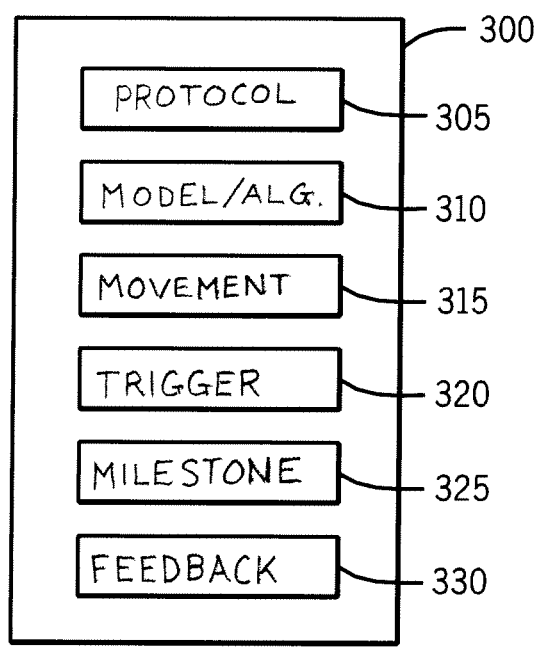
FIG. 2 illustrates a schematic diagram of an embodiment of a block of modules of program instructions to manage delivery of healthcare to the patient.

Referring to FIG. 2, an embodiment of the memory 275 includes a program package 300 comprising a plurality of modules of program instructions directed to a general structure to manage and direct feedback related to acquired data associated with completion of protocol during delivery of healthcare to the patient 110.

Module 305 includes program instructions directed receiving and creating a protocol template for each process or procedure to perform on the patient. When creating the protocol template, the module 305 can receive and store the series of tasks or steps to complete the procedure, milestones or events that demarcate progress from start to end of the procedure, resources employed in the procedure, and a predicted duration of time to complete one or more tasks or to complete the overall procedure.

Module 310 includes program instructions directed to creating or receiving mathematical models or algorithms representative of event triggers or temporal relationships or logic operable to reason or identify occurrence of the activity or step or protocol.

Module 315 includes program instructions directed to tracking, identifying or detecting the presence or movement of multiple resources in the space or suite, or the ingress/egress relative to certain created zones or volumes defined within the space, employing data received from one or more of the tracking technologies described above.

Module 320 includes program instructions directed to trigger that an event has taken place or occurred is about to occur. The mathematical models or algorithms can comprise multiple AND/OR statements according to detection of movement or presence of various resources in the space or suite being monitored with the tracking system.

Module 325 includes program instructions representative of comparator logic to track, detect or identify when a milestone event has been reached or occurred. One embodiment of the comparator logic can include AND/OR rule-based, evidentiary or artificial intelligence based logic to trigger or equate that the milestone event occurred if the tracking system provides data of evidence of the presence or movement of one or more unique or classifications of resources within the space or other smaller zone or volume described below. Computer reasoned protocol and activity steps not passing an adjustable threshold of certainty may be configured to trigger and receive clarifying feedback (e.g., verbal input or output).

Module 330 includes program instructions directed to communicating feedback for storage in the memory 275. In one example, images are not stored and the program instructions only direct communication of the computer vision renderings and reasoning.

Referring back to FIG. 1, an embodiment of the controller 200 is also connected in communication with an input device 350 and an output device 355. The input device 350 can include one or combination of a keyboard, touch-screen, remote computer workstation, mouse, joystick, tracker ball, etc. or the like operable to receive data from an operator. The output device 355 can include a display comprising one or combination of a monitor, an alarm, light emitting diodes (LEDs), printer, audible speaker, pager, personal data assistant (PDA), etc. operable to visually or audibly show an output of the controller 200 for illustration to an operator. The controller 200 can also be connected in communication with a remote computer or workstation (not shown).

The system 100 can also be connected in communication with miscellaneous other resources 105, including health information systems (HIS).

Figure 3:
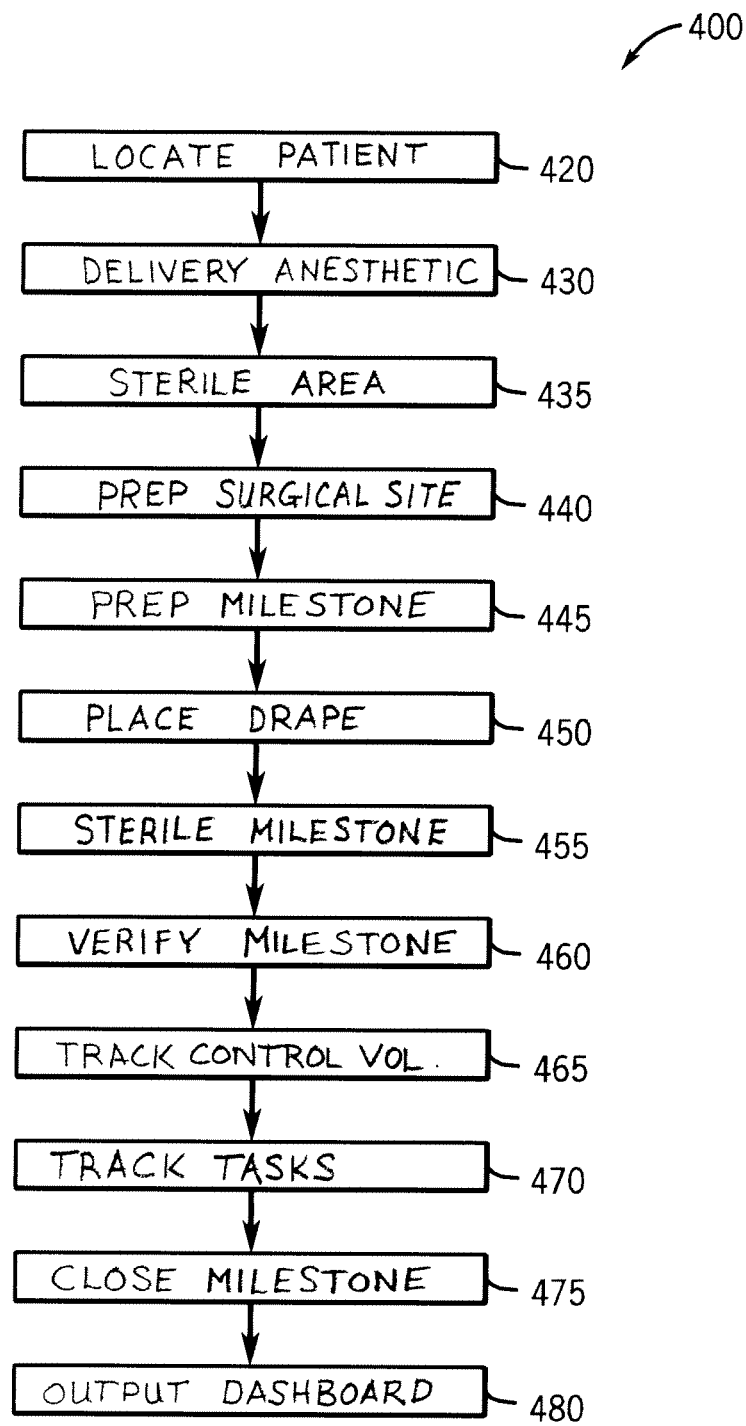
FIG. 3 shows a flow diagram of an embodiment of a method to delivery healthcare to the patient with the system of FIG. 1.

FIG. 3 includes a flow diagram to illustrate an embodiment of a method 400 of operation of the system 100 to manage workflow in a surgical suite. It should also be understood that the sequence of the acts or steps of the method 400 as discussed in the foregoing description can vary. Also, it should be understood that the method 400 may not require each act or step in the foregoing description, or may include additional acts or steps not disclosed herein. It should also be understood that one or more of the steps of the method 400 can be represented as computer-readable program instructions for execution by one or more processors 270 of the controller 200.

Assume the method 400 can be directed to the surgeon and staff 115 delivering a peri-operative procedure to the patient 110 on the table 130. Also assume that the delivery of healthcare can be defined into a succession of tasks or steps of a protocol. The succession of steps comprising the protocol can be stored in a template 405 located in a database 410 of the memory 275. The operator can update the list of resources 105 and tasks to perform the protocol of the procedure via the protocol template 405 stored in the database 410 at any time. One or more of the steps or tasks can be associated with ingress or egress of one or more resources 105 into the control volume 210 or sterile zone 215. Also, one or more of the steps of the protocol can be performed outside the control volume 210 or sterile zone 215. Each step or task of the protocol can be associated with a predicted time duration to complete, that together with all of the steps comprise a total predicted time duration to complete the protocol to deliver healthcare to the patient 110. The protocol may further include tasks or steps to complete (e.g., deliverables or room preparation, cleanup, transfer of dirty equipment to be cleaned or introduction of clean equipment to the space, etc.) even though the patient 110 may not present in a space 412 (e.g., surgical suite). Also assume that protocol includes multiple events or milestones from start to completion. One or more of the events or milestones can be associated with detection or identification of multiple tasks or detection of resources associated therewith or combination thereof. The following discussion of an example can explain in more detail.

Step 420 can include detecting or tracking the location of the patient 110 in the control zone 210 or at the table 130. The location of the patient 110 can be detected via the tracking system 195 employing one or more of the technologies (e.g., RFID, IR technology, electromagnetic transmitters, motion detectors, (e.g., at the table), voice recognition, etc.) or a combination thereof described above. Step 420 can include outputting a signal representative of a milestone 422 of protocol execution as well as that of confirming location of the patient 110 in the control volume 210 or placement on the table 130.

Step 430 can include detecting the delivery of anesthesia to the patient 110. Step 430 can include acquiring a communication signal of such from the anesthesia machine 135, or acquiring a voice recognition of an instruction of delivery of anesthesia to the patient 110, comparison of a biometric measurement (e.g., respiratory rate or heart monitor of the patient 110) relative to a threshold indicative of sedation, etc. Step 430 can include outputting a signal representative of a milestone 432 of execution of sedation of the patient 110.

Step 435 can include tracking removal of sterile or non-sterile resources 105 and 145 and no reentry thereof of contaminated resources 105 into the control volume 210. Step 435 can include tracking of staff 115 within a threshold distance of and for a threshold time relative to a hand hygiene system 436 prior to detection of entry of the staff 115 into the control volume 210 employing one or combination of the technologies of the tracking system 195 described above. Step 435 can include comparing a predicted duration (see 437 in FIG. 4) to verify removal of non-sterile items to an actual measurement of duration (see 438 in FIG. 4) to verify sterility of the control volume 210.

Step 440 can include detecting preparation of the surgical site 192 (e.g., shaving/scrubbing/application of disinfectant) on the patient 110. An embodiment of step 440 can include detection via signals acquired from the tracking system 195 (e.g., the optical technology 230, the RFID/IR technology 250, the electromagnetic technology 220, the voice recognition technology 260, etc.) indicative or representative of the staff 115 within a threshold distance of the patient 110 or table 130 or within the control volume 210 as defined by the tracking system 195. Step 440 can also include acquiring signals from the voice recognition technology or system 260 representative of key words expressed by the staff 115 indicating application or execution of shaving/scrubbing/application of disinfectant at the surgical site 192 of the patient 110.

Step 445 can include calculation and outputting a signal representative of the milestone 446 for completion of prep of the patient 110. An embodiment of step 445 can include comparison of the detected steps or tasks described above relative to the protocol to identification completion of the event or milestone 446 of prep of the patient 110 to receive delivery of healthcare (e.g., the surgical procedure). Although the event or milestone 446 of prep of the patient 110 is described with completion of one or more of the tasks or steps described above, it should be understood that the number and types of steps to associate with this or other milestones can vary in combination or include different steps than that described.

Step 450 can include detection of placement of the drape 190 over the patient 110. Step 450 can be performed upon visualization of the authorization of milestone of the prep of the patient 110 in step 445. Step 450 can include detecting entry of the drape 190 into the sterile zone 215 via one or combination of the tracking technologies described above for placement of the drape 190 over the surgical site 192 of the patient 110.

Step 455 can include detecting and outputting a signal representative of a milestone 456 for defining or establishing the sterile zone 215 over or around the surgical site 192 on the patient 110. An embodiment of the sterile zone 215 can be a three-dimensional portion of the control volume 210 or a two-dimensional plane. Outputting the signal representative of the milestone 456 can be in response to calculating according to an AND logic function representative of acquiring signals representative of completion or detection of more than one of following events: the milestone 446 for prep of the patient 110, placement of the surgical drape 190, and establishing the control volume 210.

Step 460 can include detecting or calculating and outputting a signal representative of the milestone 462 of verification of the staff 115 (e.g., surgeon, nurse, technician, etc.) to perform the procedure having a sterile state and positioned in the control volume 210 and/or positioned ready to perform the procedure. Detection of the sterile state of the staff 115 can be performed with tracking (e.g., optical, RFID, IR, electromagnetic, etc.) of the staff 115 to be present for a threshold time within a predetermined threshold distance of the hand hygiene or sterilization station 436 (See FIG. 1).

Step 465 can include dynamic tracking of the control volume 210 to detect presence of predetermined resources 105 each having a sterile state (as determined per RFID tracking of sterilization of each resource 105 relative to a cleaning station (e.g., detection of location in a cleaning room for a threshold time or within threshold distance of hand hygiene station 436 for threshold time) located therein to perform the procedure per the according to the predetermined list of resources 105 stored in the template 405 associated with the procedure and stored in the database 410 at the memory 275. Step 465 can include comparing one or more of the tracking technologies of the tracking system 195 described above to verify the identify of the resources 105 in the control volume 210.

Step 465 can include a technique referred to "counting out", where the system 100 detects and outputs a list 466 (See FIG. 4) of resources 105 (e.g., miscellaneous tools such as sponges, catheters, scalpels, etc.) that enter the sterile zone 215 counting out a list 467 (See FIG. 4) of resources 105 leaving the sterile zone 215. Step 465 further includes tracking to detect and alarm if entry of any non-sterile resources into the control volume 210 or the sterile zone 215, or if the list 467 of resources 105 leaving the sterile zone 215 does not equate to the list 466 of resources 105 that enter the sterile zone 215.

Step 465 can further include calculating and outputting a probability 468 of ingress or egress of one or more resources 105 to or from the sterile zone or control volume. The probability 468 can be calculated dependent in a predetermined manner or algorithm (e.g., linear relationship, logarithmic relationship, exponential, weighted according to predetermined factors assigned to tracking technologies, other parametric relationship, etc.) according to a number of and type (e.g., RFID/IR system 250 may be more reliant on detection than optical system 230) of technologies operable to track movement of the resource 105. The probability 468 can also increase in a manner described above with detection via voice recognition of reference of the resource 105 relative to point in time of ingress or egress to the control volume 210 or sterile zone 215, and relative to identification of the resources 105 in the list as stored in the protocol template 405 to perform the identified task occurring or for the overall procedure or process to deliver healthcare to the patient 110.

Step 470 can include employing one or combination of the tracking technologies (e.g., electromagnetic tracking system 220, optical tracking system 230, voice recognition system 260, GPS tracking system 225, RFID/IR system 250, etc.) of the tracking system 195 to identify and output signals representative of completion of miscellaneous predetermined tasks or milestones of the procedure or process toward completion, as listed or described in the protocol template 405.

Step 475 can include detecting and outputting the milestone 476 of ready or start to close the surgical site 192 of the patient 110. Step 475 can include calculating the milestone 476 to equate to an AND logic function of receiving authorization of completion of step 465 and acquiring signals representative of completion of the tasks of the procedure as described in step 470.

Step 480 can include outputting a dashboard 500 (See FIG. 4) including a temporal display of a predicted time and a measured time to reach each milestone in the procedure described above for illustration at the output device 355 (See FIG. 1). This step 480 can occur continuously from prior to start of the procedure to conclusion of the procedure, providing updates to a central or remote workstation of changes in predicted durations to deliver healthcare to patients 110, changes to predicted time to complete, and to display alerts to impact of updated duration of time of use of resources 105 and later cleanup relative to subsequent scheduling of the resources 105 for use in delivery of healthcare on other patients 110.

Figure 4:
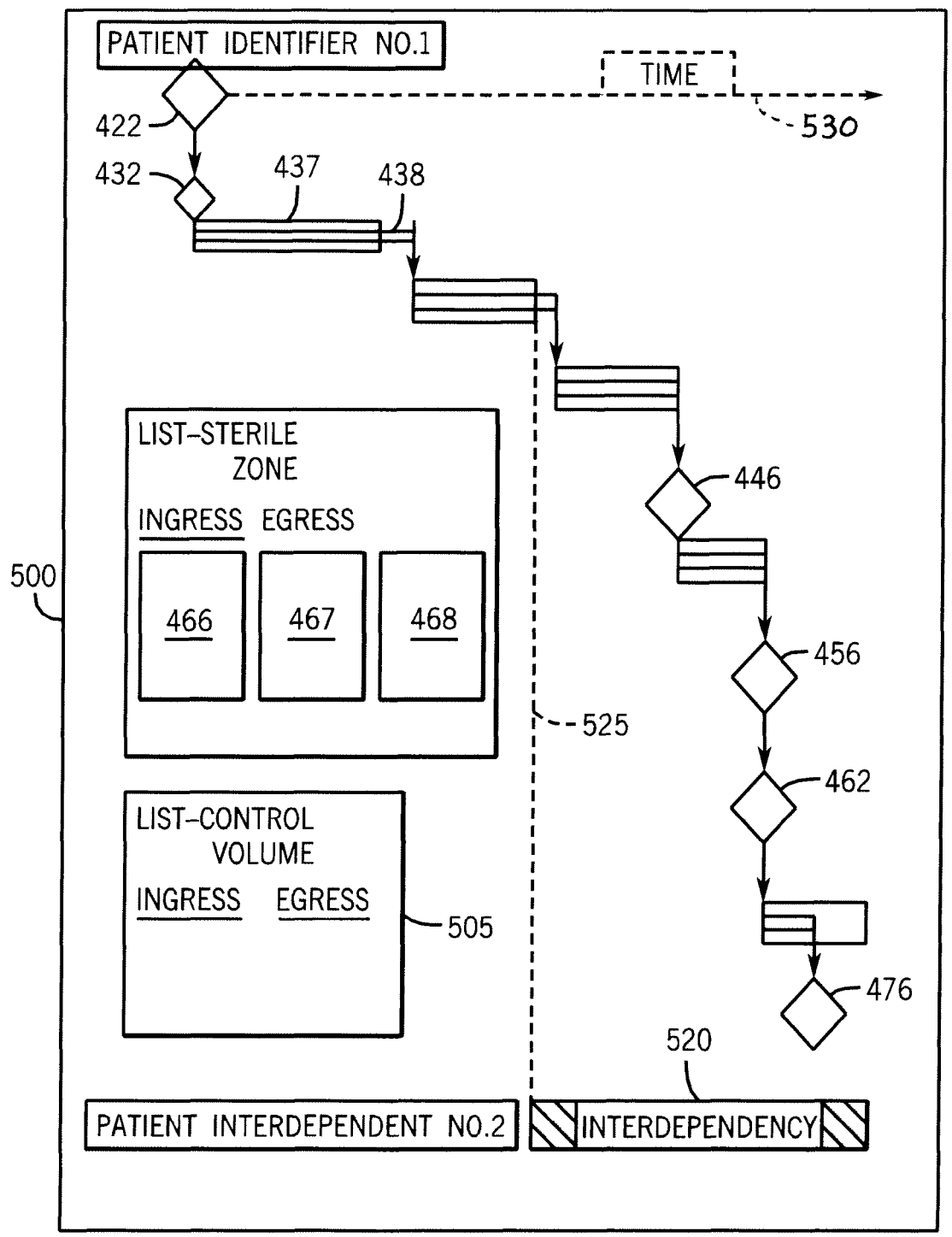
FIG. 4 shows a schematic diagram of an embodiment of a dashboard illustrative of performance of the system of FIG. 1 and method of FIG. 3.

FIG. 4 shows an embodiment of the output of data from the system 100 for illustration in the dashboard 500 in managing the delivery of healthcare to the patient 110. The dashboard 500 can include graphic representations of one or more of the milestones or events or tasks of the method 300 described above, including: milestone 422 for entry of patient into the space, milestone 432 for sedation of patient 110, milestone 446 for prep of the patient 110, defining the control volume 210, milestone 456 for creating sterile plane or zone 215, milestone 462 for positioning of staff 115 ready (e.g., sterile) to perform procedure, step of counting out resources 105 employed in performing the procedure on or delivery of healthcare to the patient 110, milestone 476 of ready to close of surgical site 192 on patient 110, predicted duration of time 437 between each milestone event, measured or actual time 438 between each milestone event, list 505 of ingress or egress of resources 105 to or from the control volume 210, list 466, 467 of ingress or egress of resources 105 detected to or from the sterile zone 215, and graphic illustrations of an interdependency 520 of resources 105 to their forward or later or subsequent schedule of use or location or combination thereof in performance of procedures on other patients 110. It should be understood that the type and number of graphic representations comprising the dashboard 500 can vary.

An example of a technique to identify interdependencies in the scheduling of resources 105 is described in U.S. patent application Ser. No. 112/040,646 to Johnson et al, entitled "Method To View Schedule Interdependencies and Provide Proactive Clinical Process Decision Support in Day View Form", filed on Feb. 29, 2008 and hereby incorporated herein by reference in its entirety. Visualization of interdependency 520 in the scheduling or predicted or actual timed events 437, 438 or milestones 422, 432, 456 of performance of the resources 105 (see FIG. 1) can be illustrated as a critical path (see dashed line and reference 525). Tasks and the resources 105 (e.g., people, equipment, consumables, medications, disposables, etc.) to perform the tasks in accordance to the protocol can be predetermined and listed in association with template 405 (See FIG. 1) so as direct scheduling of the resources 105 prior to delivery of care to the patient 110. The dashboard 500 can generally illustrate how the system 100 maps the precedence of tasks to perform the protocol relative to a time scale (see dashed line and reference 530) in the scheduling of the resources 105 to deliver healthcare to multiple patient 110 over an extended period (e.g., day) in association with predictions of the durations of tasks to be completed with the resources 105. Forecast scheduling of resources 105 and predicted durations of tasks 437 can be updated manually or statistically over time with enabling the providers of care to become aware of where delays and variances occur.

The dashboard 500 can further include a comparison of tracking of actual completion of events 438 or milestones 422, 432, 456 relative to list of tasks or milestones as described in protocol template 405, actual or measured time of occurrence or duration 438 of events or tasks relative to the prediction 437 of time or duration of events or tasks, or a comparison of the tracking of spatial distribution of resources 105 and defined control volume 210 or sterile zone 215 (see FIG. 1) relative to a predicted spatial distribution thereof according to data acquired by the tracking system 195 in comparison to predetermined spatial distribution as described or stored in the protocol template 405.

The system 100 and method 400 can employ multiple tracking technologies, mathematical modeling techniques, and comparative logic rules to output the visualization for illustration. Another technical effect of the system 100 and method 400 can include tracking and comparing the predetermined protocol standard relative to actual events of protocol, time of events of protocol, and standard versus spatial distribution of resources 105 and output feedback of comparison for illustration. Another technical of the system 100 and method 400 can include providing the above-described technical effects of tracking and comparing in low-intrusive or low-interruptive manner that minimally interferes with the performance of the resources 105 executing the protocol.

One or more elements or constructions of one or more embodiments of the subject matter described above may be combined with one or more elements or constructions of other embodiments of the subject matter described above and is not limiting on the subject matter described herein.

A technical effect of the subject matter described herein can include providing the system 100 and method 400 and dashboard 500 to visualize location and scheduling of the resources 105 (e.g., assets, people, consumables, apparatus and etc.) in the delivery of healthcare to patients. The system 100 and method 200 and dashboard 500 can identify of problems (e.g., delays, missed protocol, etc.) and the interdependence, status and relationship of the resources 105 to the execution of protocol scheduled in the future delivery of the healthcare to patients 110.

Another technical effect can include providing the system 100 and method 200 output proposed actionable decisions or to automatically trigger actionable decisions in scheduling or execution of protocol in response to the detection of problems in the delivery of healthcare to patients. This technical effect can be realized with visualization of the interdependencies of the resources 105 in the past, present and future, as well as visualization of the past, present and scheduled or predicted future status (e.g., locations, scheduled cleaning, scheduled breaks, scheduled unavailability of staff, etc.) of the resources 105 so as to simulate and visualization of potential or predicted scenarios in the scheduling of resources 105. For example, the system 100 or method 200 can simulate of the scheduling and execution of protocol by the resources 105 so as to allow care providers to scroll forward to uncover potential bottlenecks in the future schedule and to receive list of alternative action options (e.g., list of alternate available resources 105 and locations). The system 100 and method 200 can also calculate or output a confidence or probability in the simulation of the schedule of resources 105. An embodiment of the system 100 and method 200 can further output alerts to problems (e.g., delays, low confidence, etc.) and interdependencies of scheduled resources 105 upon comparison to acceptable or unacceptable thresholds of variation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of managing delivery of healthcare via a plurality of resources to a patient, the method comprising:
    tracking and outputting, using a processor, a signal representative of a location of at least one of the plurality of resources relative to a control volume defining a space associated with the patient and registered relative to a fixed reference prior to delivery of care to the patient, the resources associated with a selected healthcare delivery protocol defining a plurality of milestones, each milestone associated with a plurality of tasks involving one or more resources, the selected healthcare delivery protocol associated with the patient;
    acquiring, using the processor, at least one signal representative of detecting ingress or egress of at least one of the plurality of resources relative to the control volume during execution of the selected healthcare delivery protocol;
    comparing, using the processor, the at least one signal representative of detecting ingress or egress of at least one of the plurality of resources relative to the control volume to the plurality of tasks associated with the selected healthcare delivery protocol associated with the patient to determine completion of a milestone of the selected healthcare delivery protocol; and
    outputting, using the processor, a first signal representative of one of the plurality of milestones as defined in the selected protocol in response to detecting ingress or egress of at least one of the plurality of resources relative to the control volume while applying the selected protocol with respect to the patient and determining completion of the milestone; and
    tracking, using the processor, execution of the selected healthcare delivery protocol based on the completion of milestones associated with the selected healthcare delivery protocol and providing feedback regarding the execution of the selected healthcare delivery protocol.

2. The method of claim 1, wherein tracking includes outputting at least one signal representative of an ingress or an egress of at least one resource relative to a sterile zone within the control volume.

3. The method of claim 1, wherein tracking is performed by more than one of the following: an optical tracking system, an electromagnetic tracking system, an RFID tracking system, an IR tracking system, a GPS tracking system, and a voice recognition system, and wherein tracking includes outputting at least one signal representative of ingress or egress of one of the plurality of resources relative to a sterile zone located within the control volume.

4. The method of claim 3, further comprising outputting a probability of ingress or egress of at least one of the plurality of resources relative to the sterile zone, the probability dependent on how many of or which of the different tracking systems detects ingress or egress of the at least one of the plurality of resources relative to the sterile zone.

5. The method of claim 4, wherein outputting the probability is dependent on a mathematical expression having a first factor associated with detecting ingress or egress of the at least one of the plurality of resources relative to the sterile zone with a first tracking system and a second factor associated with detecting ingress or egress of the at least one of the plurality of resources relative to the sterile zone with a second tracking system different than the first tracking system.

6. The method of claim 3, further comprising: outputting a comparison of ingress of at least one of the plurality resources to a sterile zone defined within the control volume relative to egress of at least one of the plurality of resources from the sterile zone, the ingress and egress as detected by one of the tracking systems.

7. The method of claim 1, further comprising: outputting a second signal representative of another of the plurality of milestones as defined in the selected healthcare delivery protocol in response to outputting the first signal; in combination with one of the following: detecting ingress or egress of another of the plurality of resources relative to the control volume, and detecting a key text in a translation of an audio recording where the key text is associated with executing the another of the plurality of milestones and predetermined in a protocol template for storage in a database.

8. The method of claim 1, further comprising: outputting a comparison of a predicted time for the milestone to occur relative to a measured time of occurrence of outputting the first signal representative of the milestone.

9. The method of claim 1, wherein the milestone is representative of one of the following: preparation of the patient to receive a medical procedure, sedation of the patient to receive the medical procedure, and close of the surgical site on the patient.

10. A system to manage delivery of healthcare via a plurality of resources to a patient, the system comprising:
    at least one tracking system operable to generate a signal representative of a location of at least one of the plurality of resources relative to a control volume defining a space associated with the patient and registered relative to a fixed reference prior to delivery of care to the patient; and
    a controller in communication with the tracking system, the controller including a processor in communication with a memory, the processor operable to execute a plurality of program instructions stored in the memory, the plurality of program instructions representative of:
        acquiring at least one signal representative of detecting ingress or egress of at least one of the plurality of resources relative to the control volume during execution of the selected healthcare delivery protocol;
        comparing the at least one signal representative of detecting ingress or egress of at least one of the plurality of resources relative to the control volume to the plurality of tasks associated with the selected healthcare delivery protocol associated with the patient to determine completion of a milestone of the selected healthcare delivery protocol;
        outputting a first signal representative of one of the plurality of milestones as defined in the selected protocol in response to detecting ingress or egress of at least one of the plurality of resources relative to the control volume while applying the selected protocol with respect to the patient and determining completion of the milestone; and
        tracking execution of the selected healthcare delivery protocol based on the completion of milestones associated with the selected healthcare delivery protocol and providing feedback regarding the execution of the selected healthcare delivery protocol.

11. The system of claim 10, wherein the tracking system comprises more than one of the following: an optic tracking system, an electromagnetic tracking system, an RFID tracking system, an IR tracking system, a GPS tracking system, and a voice recognition system, and wherein the tracking system generates at least one signal representative of ingress or egress of one of the plurality of resources relative to a sterile zone located within the control volume.

12. The system of claim 11, further comprising program instructions representative of calculating a probability of ingress or egress of at least one of the plurality of resources relative to the sterile zone, the probability dependent on how many of or which of the different tracking systems detects ingress or egress of the at least one of the plurality of resources relative to the sterile zone.

13. The system of claim 12, wherein outputting the probability is dependent on a mathematical expression having a first factor associated with detecting ingress or egress of the at least one of the plurality of resources relative to the sterile zone with a first tracking system and a second factor associated with detecting ingress or egress of the at least one of the plurality of resources relative to the sterile zone with a second tracking system different than the first tracking system.

14. The system of claim 10, further comprising program instructions representative of: outputting a comparison of ingress of at least one of the plurality resources to a sterile zone defined within the control volume relative to egress of at least one of the plurality of resources from the sterile zone, the ingress and egress as detected by the tracking system.

15. The system of claim 10, further comprising program instructions representative of outputting a second signal representative of another of the plurality of milestones as defined in the selected healthcare delivery protocol in response to outputting the first signal, and in combination with at least one of the following: detecting ingress or egress of another of the plurality of resources relative to the control volume, and detecting a key text in a translation of an audio recording where the key text is associated with executing the another of the plurality of milestones and predetermined in a protocol template for storage in a database.

16. The system of claim 10, further comprising program instructions representative of outputting a comparison of a predicted time for the milestone to occur relative to a measured time of occurrence of outputting the first signal representative of the milestone.

17. The system of claim 10, further comprising an program instructions representative of: calculating a variation between a difference in a predicted schedule of time of use of the resource and an actual time of use of the resource relative to a threshold; and outputting an interdependency of the scheduled time of use of the resource for the patient relative to another scheduled time of use of the resource for another patient in response to calculating the variation exceeds the threshold.

18. The system of claim 10, wherein the milestone is representative of one of the following: preparation of the patient to receive a medical procedure, establishment of a sterile field, sedation of the patient to receive the medical procedure, and close of a surgical site on the patient.

* * * * *